(12) United States Patent
Croft

(10) Patent No.: US 7,160,294 B2
(45) Date of Patent: Jan. 9, 2007

(54) SYSTEMS AND METHODS FOR TREATING HEMORRHOIDS

(75) Inventor: Rachel Croft, San Francisco, CA (US)

(73) Assignee: Curon Medical, Inc., Fremont, CA (US)

( * ) Notice: Subject to any disclaimer, the term of this patent is extended or adjusted under 35 U.S.C. 154(b) by 0 days.

(21) Appl. No.: 10/653,448

(22) Filed: Sep. 2, 2003

(65) Prior Publication Data
US 2005/0049660 A1    Mar. 3, 2005

(51) Int. Cl.
*A61B 18/18*    (2006.01)
(52) U.S. Cl. .................. 606/41; 607/101; 607/133
(58) Field of Classification Search .......... 606/41, 606/45, 49, 50; 607/101–102, 133; 604/22, 604/506
See application file for complete search history.

(56) References Cited

U.S. PATENT DOCUMENTS

| | | | |
|---|---|---|---|
| 2,382,109 A | | 8/1945 | Sheiffele |
| 4,898,169 A | * | 2/1990 | Norman et al. ............... 606/42 |
| 5,370,675 A | | 12/1994 | Edwards et al. |
| 5,403,311 A | | 4/1995 | Abele et al. |
| 5,451,223 A | | 9/1995 | Ben-Simhon |
| 5,709,224 A | | 1/1998 | Behl et al. |
| 5,827,276 A | | 10/1998 | LeVeen et al. |
| 5,849,011 A | | 12/1998 | Jones et al. |
| 5,873,877 A | | 2/1999 | McGaffigan et al. |
| 5,957,920 A | | 9/1999 | Baker |
| 6,006,755 A | | 12/1999 | Edwards |
| 6,009,877 A | | 1/2000 | Edwards |
| 6,014,589 A | | 1/2000 | Farley et al. |
| 6,017,338 A | | 1/2000 | Brucker et al. |
| 6,024,742 A | * | 2/2000 | Tu et al. ....................... 606/41 |
| 6,044,846 A | | 4/2000 | Edwards |
| 6,056,744 A | | 5/2000 | Edwards |
| 6,073,052 A | | 6/2000 | Zelickson et al. |
| 6,077,257 A | | 6/2000 | Edwards et al. |
| 6,092,528 A | | 7/2000 | Edwards |
| 6,206,842 B1 | * | 3/2001 | Tu et al. ........................ 601/2 |
| 6,231,571 B1 | | 5/2001 | Ellman et al. |
| 6,254,598 B1 | | 7/2001 | Edwards et al. |
| 6,325,798 B1 | | 12/2001 | Edwards et al. |
| 6,419,673 B1 | | 7/2002 | Edwards et al. |
| 6,425,877 B1 | | 7/2002 | Edwards |
| 6,464,689 B1 | | 10/2002 | Qin et al. |
| 6,464,697 B1 | | 10/2002 | Edwards et al. |
| 6,530,878 B1 | * | 3/2003 | Silverman et al. ........... 600/29 |
| 6,544,226 B1 | | 4/2003 | Gaiser et al. |
| 6,547,776 B1 | | 4/2003 | Gaiser et al. |
| 6,589,238 B1 | | 7/2003 | Edwards et al. |
| 6,645,201 B1 | * | 11/2003 | Utley et al. .................. 606/41 |
| 2002/0115992 A1 | | 8/2002 | Utley et al. |
| 2002/0133214 A1 | | 9/2002 | Baker |
| 2002/0156470 A1 | | 10/2002 | Shadduck |

(Continued)

FOREIGN PATENT DOCUMENTS

WO    WO 9811834    3/1998

(Continued)

*Primary Examiner*—Roy D. Gibson
(74) *Attorney, Agent, or Firm*—Ryan Kromholz & Manion, S.C.

(57) ABSTRACT

Systems and methods treat hemorrhoids by introducing a treatment device into the anal canal to extend above a hemorrhoidal plexus and adjacent a tissue region containing blood vessels that feed the hemorrhoidal plexus. The systems and methods operate the treatment device to affect tissue morphology in the tissue region to occlude or otherwise reduce blood flow through the vessels.

3 Claims, 7 Drawing Sheets

| U.S. PATENT DOCUMENTS | | | | | |
|---|---|---|---|---|---|
| 2003/0055421 A1 | 3/2003 | West et al. | WO | WO 01/05318 | 1/2001 |
| | | | WO | WO 02/076541 | 10/2002 |

FOREIGN PATENT DOCUMENTS

| WO | WO 0059393 | 10/2000 |
|---|---|---|

* cited by examiner

SYSTEMS AND METHODS FOR TREATING HEMORRHOIDS

RELATED APPLICATIONS

This application claims the benefit of application Ser. No. 09/556,169, filed Apr. 21, 2000, entitled "Systems and Methods for Treating Dysfunctions in the Intestines and Rectum," which is incorporated herein by reference.

FIELD OF THE INVENTION

The invention relates generally to systems and methods for treating interior tissue regions of the body. In particular, this invention relates to the treatment of hemorrhoids.

BACKGROUND OF THE INVENTION

Hemorrhoids are cushions of tissue and varicose veins located in and around the rectal area. Hemorrhoids are very common, especially during pregnancy and after childbirth. It has been estimated that about half the population has hemorrhoids by age 50. They are caused by increased pressure in the veins of the anus. The most common cause is straining during bowel movements. Constipation, prolonged sitting during bowel movements, and anal infection may also contribute to the development of hemorrhoids. In some cases, hemorrhoids may be a manifestation of other diseases, such as liver cirrhosis.

Symptoms of hemorrhoids include rectal bleeding, particularly after bowel movements, pain during bowel movements, anal itching, mucus discharge, epithelial cell changes, thrombosis, incarcerations, skin tags, and disordered defecation. Symptoms may range from mild to severe.

In many cases, hemorrhoids are diagnosed by rectal examination. However, stool guaiac testing for the presence of occult blood, as well as sigmoidoscopy, anoscopy, and proctoscopy procedures may also be useful in establishing a diagnosis.

Treatment is generally based on the severity of symptoms. Mild cases may be controlled by conservative, non-invasive techniques such as drinking fluids, adhering to a high-fiber diet, use of stool softeners, and/or use of stool-bulking agents such as fiber supplements. In addition, treatments for symptomatic relief may include corticosteroid cream and/or warm baths to reduce pain and swelling.

For more severe cases involving severe pain and itching in patients who have not responded to conservative therapy, surgical intervention may be required to prevent more serious complications. For example, frequent or prolonged bleeding may result in iron deficiency anemia.

Conventional surgical techniques may be generally classified in three categories as being directed to either the anal sphincter, the hemorrhoidal tissue, or to the hemorrhoid feeding vessels. Surgical procedures directed to stretching or cutting of the internal anal sphincter include Lord's procedure, incisional sphincterotomy, and closed lateral anal sphincterotomy. However, these procedures may result in incontinence and thus are rarely indicated.

Surgical procedures directed to hemorrhoidal tissue include excisional hemorrhoidectomy and laser-assisted hemorrhoidectomy. Such procedures are relatively invasive and thus have a longer recovery period.

Surgical procedures directed to the feeder vessels include elastic or rubber band ligation, sclerosis, and photocoagulation. These procedures are associated with a variety of complications, including infection, hemorrhage, ulceration, oleogranuloma, allergic reaction, and prostate infection.

The need remains for minimally-invasive systems and methods for treating hemorrhoids.

SUMMARY OF THE INVENTION

The invention provides systems and methods that treat hemorrhoids. The systems and methods introduce a treatment device into the anal canal to extend above a hemorrhoidal plexus and adjacent a tissue region containing blood vessels that feed the hemorrhoidal plexus. The systems and methods operate the treatment device to affect tissue morphology in the tissue region to occlude or otherwise reduce blood flow through the vessels.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

I. Anatomy of the Rectum and Anal Canal

Figure 1:
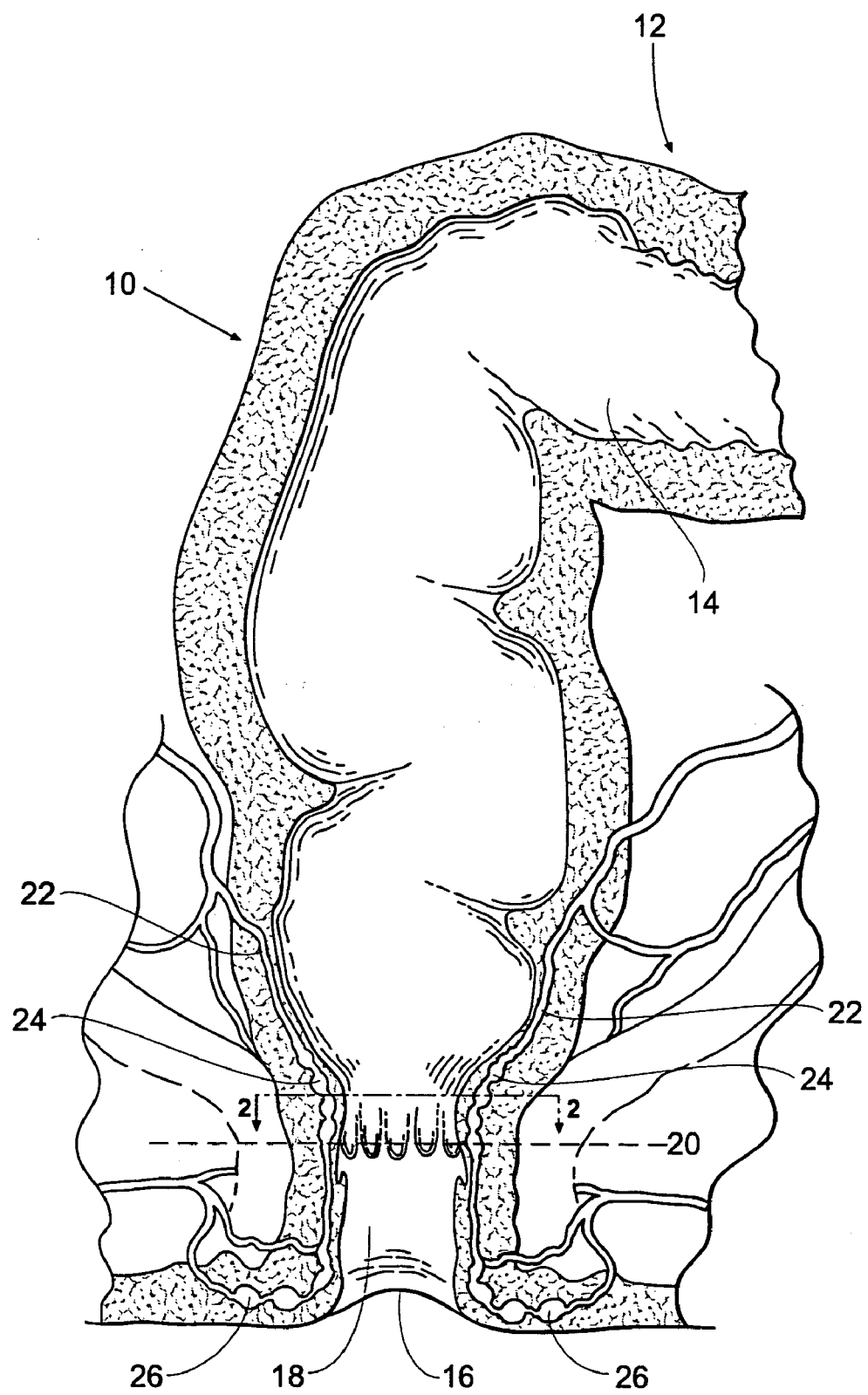
FIG. 1 is an anatomical view of the rectum and anal canal.

As FIG. 1 shows, the rectum 10 is the terminal part of the large intestine 12. The rectum 10 extends from the sigmoid flexure 14 (which is the narrowest part of the colon) to the anal orifice 16. The rectum 10 is about 15 to 17 cm in overall length.

The lower or inferior portion of the rectum 10 is called the anal canal 18. It typically extends about 4 to 5 cm above the anal orifice 16. A visible line of demarcation between tissue, called the pectinate (dentate) line 20, exists about 2.5 to 3 cm above the anal orifice 16.

Figure 2:
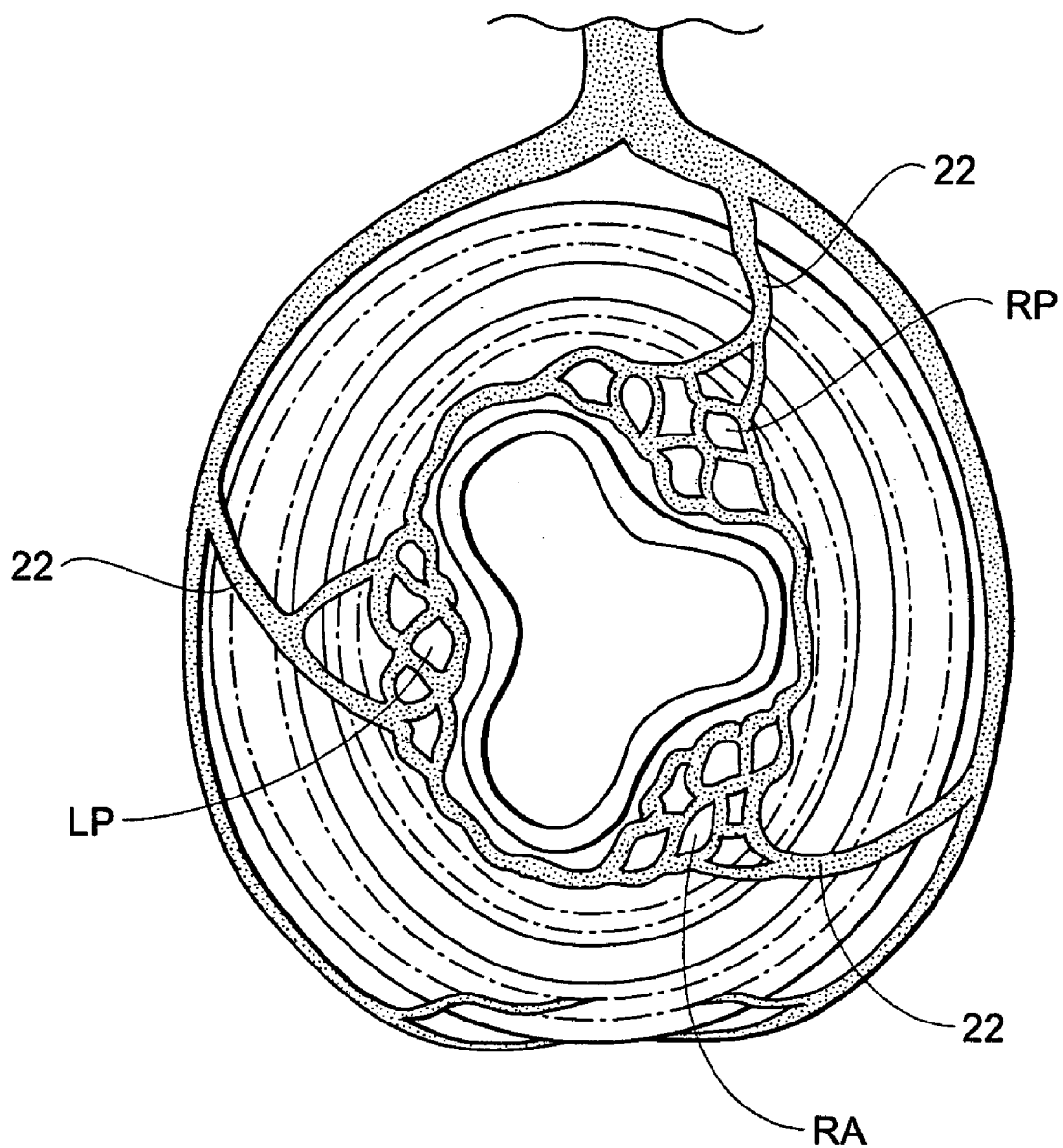
FIG. 2 is a section view taken along line 2—2 in FIG. 1.
Figure 3:
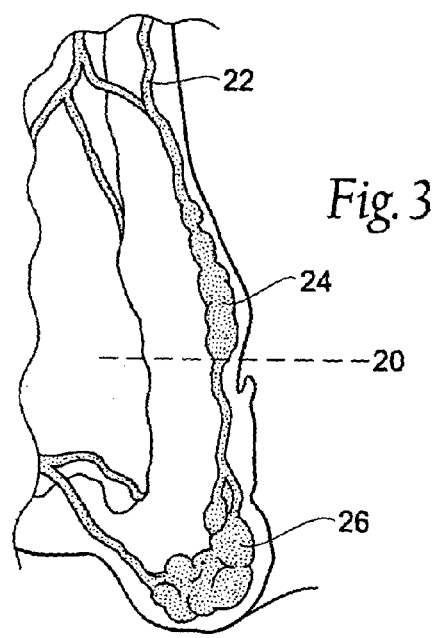
FIG. 3 is an anatomical view of an external hemorrhoid.

As best seen in FIG. 2, feeder vessels 22 descend to the anal canal 18 in three locations, the right posterior (RP), right anterior (RA), and left posterior (LP). Each of the three locations (RP, RA, and LP) then splits to form an internal hemorrhoidal plexus (or cushion) 24 (see FIG. 3) located above the dentate line 20 and an external hemorrhoidal plexus (or cushion) 26 located below the dentate line 20. That is, there are three internal hemorrhoidal plexes 24 (RP, RA, and LP) located above the dentate line 20 and three external hemorrhoidal plexes 26 (RP, RA, and LP) located below the dentate line 20.

Figure 4:
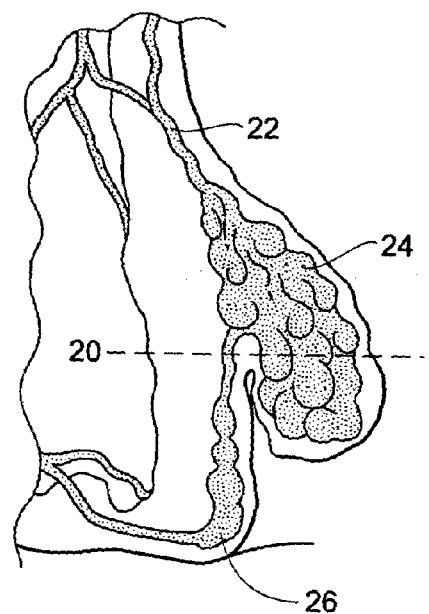
FIG. 4 is an anatomical view of an internal hemorrhoid.
Figure 5:
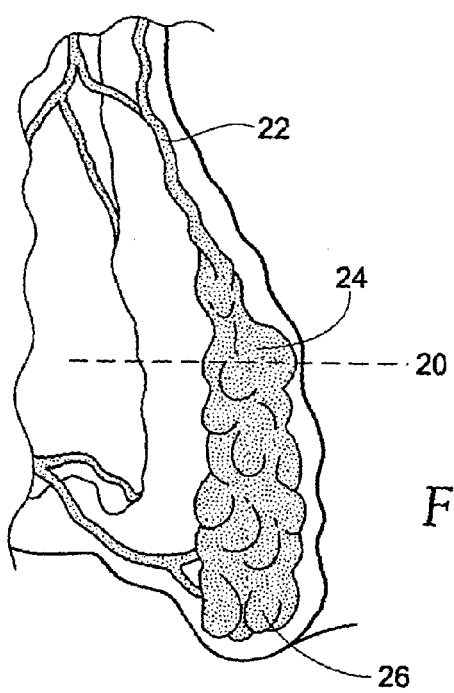
FIG. 5 is an anatomical view of a mixed internal and external hemorrhoid.

Increased pressure in the veins of the anus causes the enlargement and swelling of one or more hemorrhoidal plexes 24 or 26. This inflamed state is commonly referred to as a hemorrhoid (or pile). When the inflammation occurs in a hemorrhoidal plexus 26 below the dentate line 20 at the anal opening 16, it is referred to as an external hemorrhoid, shown in FIG. 3. When the inflammation occurs in a hemorrhoidal plexus 24 above the dentate line 20 near the beginning of the anal canal 18, it is referred to as an internal hemorrhoid, shown in FIG. 4. In some cases, a mix of internal and external hemorrhoids may be present, as illustrated in FIG. 5. A hemorrhoid may even protrude outside the anus.

It should be noted that the views of the rectum 10 and anal canal 18 shown in FIG. 1, and elsewhere in the drawings, are not intended to be strictly accurate in an anatomic sense. The drawings show the rectum 10 and anal canal 18 in somewhat diagrammatic form to demonstrate the features of the invention.

II. System Overview

Figure 6:
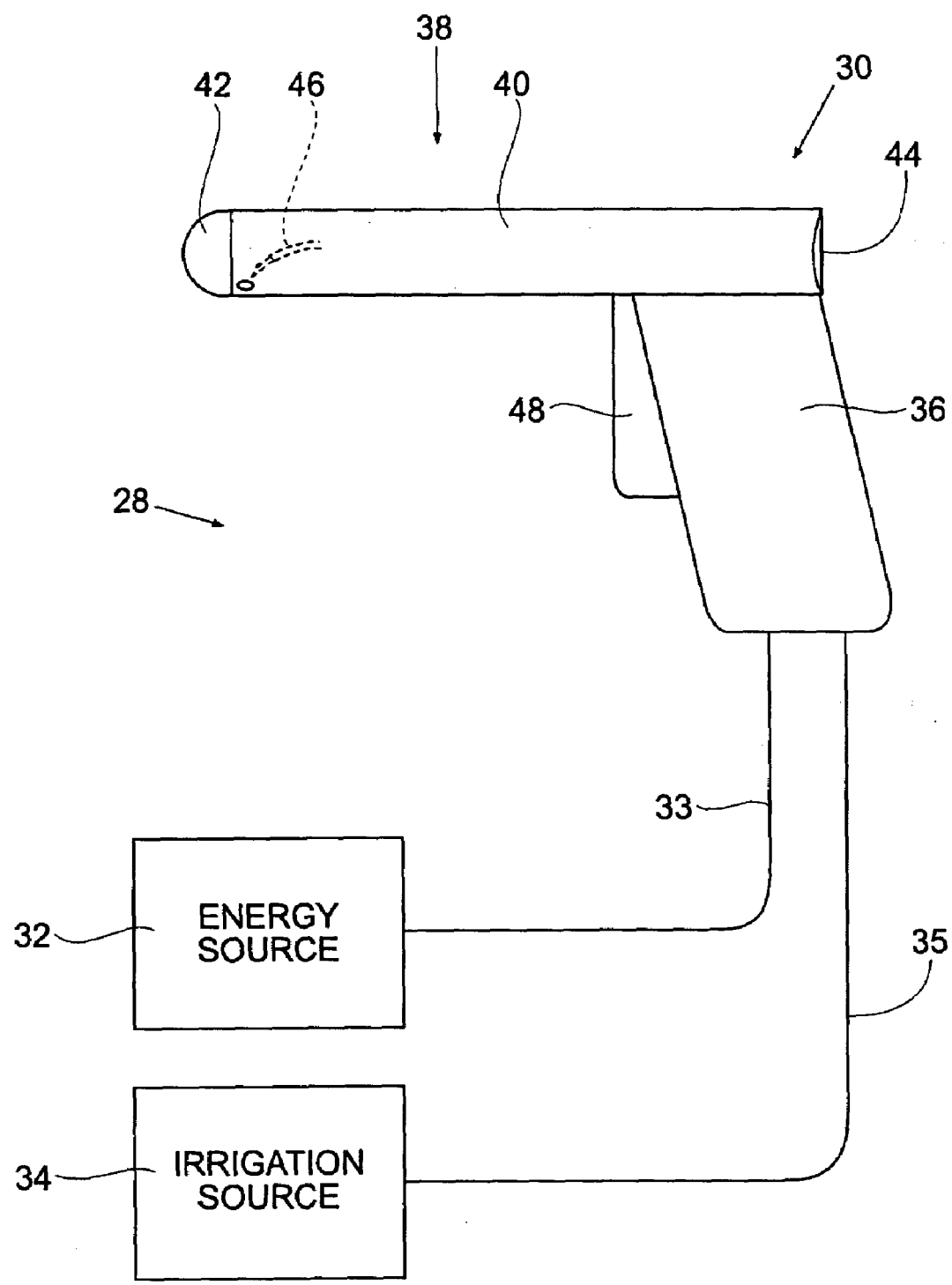
FIG. 6 is a schematic view of a system for treating hemorrhoids that includes a treatment device with a tissue-piercing member.

A tissue treatment system 28 that embodies features of the invention is shown in FIG. 6. The tissue treatment system 28 includes a tissue treatment device 30. The treatment device 30 is sized and configured to affect tissue morphology above the dentate line 20, to occlude or otherwise reduce blood flow through one or more feeder vessels for one or both hemorrhoidal plexus 24 or 26.

The treatment device 30 can affect tissue morphology by different physiologic mechanisms. For example, the treatment device 30 can serve to inject an agent used to seal vascular access sites, e.g., collagen or PEG hydrogel material—or to place a material that cause blood to clot, e.g., platinum coils deployed at the site of an aneurysm. In the illustrated embodiment, heat is applied to shrink tissue. In this arrangement, the treatment device 30 is coupled to a source of energy 32 by cable 33. If desired, the system 28 can also include certain auxiliary processing equipment. In the illustrated embodiment, the auxiliary processing equipment comprises an external fluid delivery or irrigation source 34 coupled to the treatment device 30 by tubing 35.

A. The Tissue Treatment Device

The tissue treatment device 30 serves to deliver energy to tissue regions at or near feeder vessels 22 above the internal or external hemorrhoidal plexes 24 and 26 to occlude or otherwise reduce the blood supply to the hemorrhoidal plexes 24 and 26. In the illustrated embodiment, the energy source 32 supplies radiofrequency energy. It is contemplated that other forms of energy can be applied, e.g., coherent or incoherent light, heated or cooled fluid, resistive heating, microwave, ultrasound, a tissue ablation fluid, or a cryogenic fluid. Energy is delivered submucosally to heat targeted feeder vessel regions to create scar tissue and shrink tissue, thereby occluding or otherwise reducing blood flow through a vessel or vessels 22. By occluding or otherwise reducing blood supply from above the hemorrhoidal plexes 24 or 26, blood is essentially prevented from pooling in the vessels 22 and the hemorrhoidal plexes 24 or 26. Since blood is prevented from pooling, hemorrhoids are shrunk or prevented.

As FIG. 6 shows, the tissue treatment device 30 includes a handle or hand grip 36 that carries an operative element 38. In the illustrated embodiment, the operative element 38 takes the form of a hollow tubular barrel 40, although it should be appreciated that a semi-circular device, e.g., shaped like curved tongue depressor, could be used as well. In the illustrated embodiment, the barrel 40 may be made from a transparent, molded plastic material or other suitable material to enable visualization through the barrel 40. The barrel 40 terminates with a blunt, rounded distal working end 42 to aid passage of the barrel 40 through the anal canal 18 without need for a separate introducer. The hand grip 36 desirably includes a viewing port 44 for looking into the transparent, hollow interior of the barrel 40 to visualize surrounding tissue.

The hand grip 36 and operative element 38 can form an integrated construction intended for single use and subsequent disposal as a unit. Alternatively, the hand grip 36 can comprise a nondisposable component intended for multiple uses. In this arrangement, the operative element 38 comprises a disposable assembly, which the physician releasably connects to the hand grip 36 at the time of use and disconnects and discards after use. The proximal end of the barrel 40 can, for example, include a male plug connector that couples to a female plug receptacle on the hand grip 36.

Figure 7:
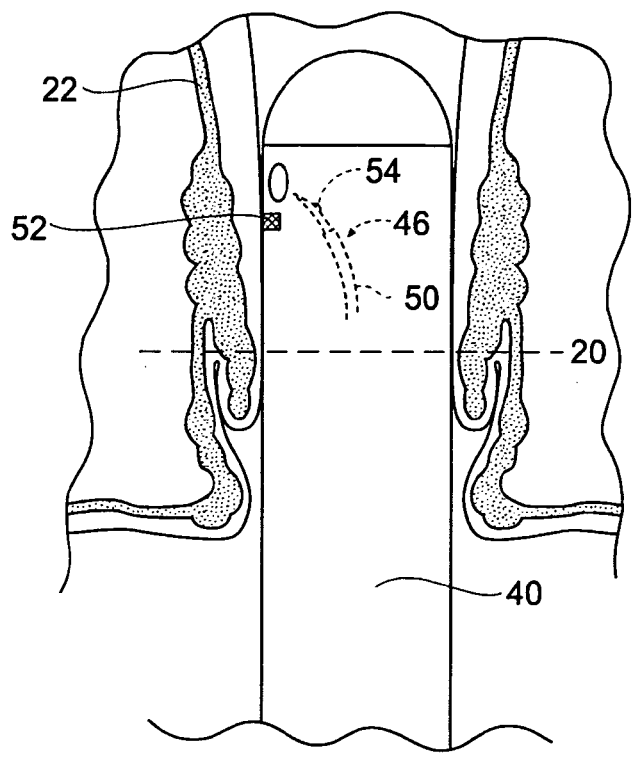
FIG. 7 illustrates a treatment device deployed in the anal canal with the tissue-piercing member in a retracted position.
Figure 8:
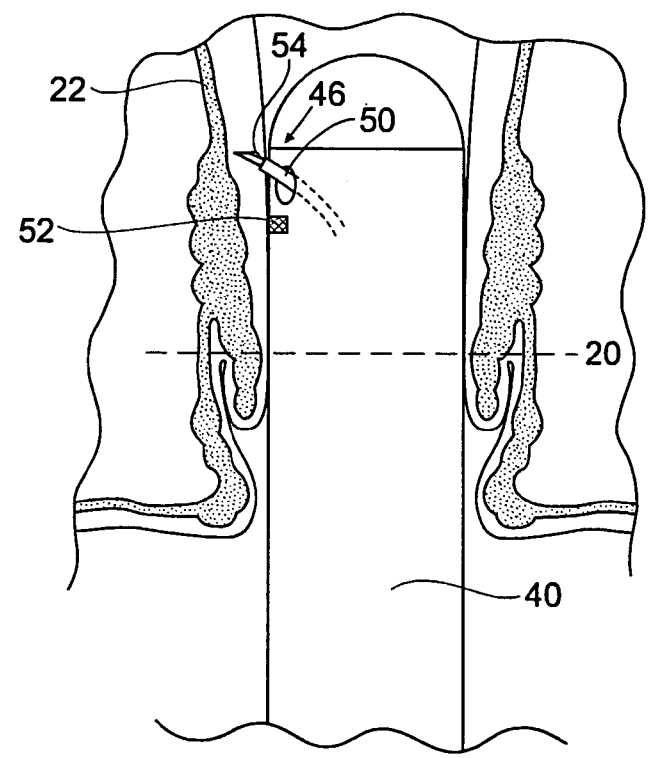
FIG. 8 is a view similar to FIG. 7 and illustrating the tissue-piercing member piercing tissue containing blood vessels that feed the internal and external hemorrhoidal plexes.

With reference to FIGS. 7 and 8, a tissue-piercing member 46 is movably contained within the barrel 40. In the illustrated embodiment, the tissue-piercing member 46 takes the form of a needle electrode. The electrode 46 is selectively movable between a retracted position (FIG. 7) and an extended position (FIG. 8). Means are provided for moving the electrode 46 between the retracted and extended positions. For example, the needle electrode 46 can be mechanically linked to a finger-operated pull lever 48 on the hand grip 36. By operation of the pull lever 48, the distal ends of the needle electrodes 46 are moved between the retracted position and the extended position. An electrical insulating material 50 is desirably coated about the needle electrodes 46, except for a prescribed region of the distal ends, where radio frequency energy is applied to tissue.

Figure 9:
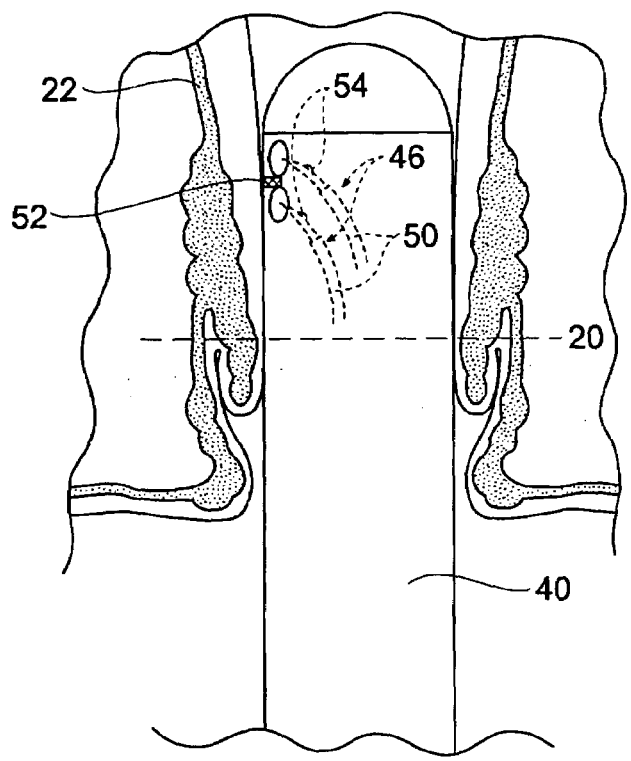
FIG. 9 illustrates a treatment device with multiple tissue-piercing members deployed in the anal canal and having multiple tissue-piercing members in a retracted position.
Figure 10:
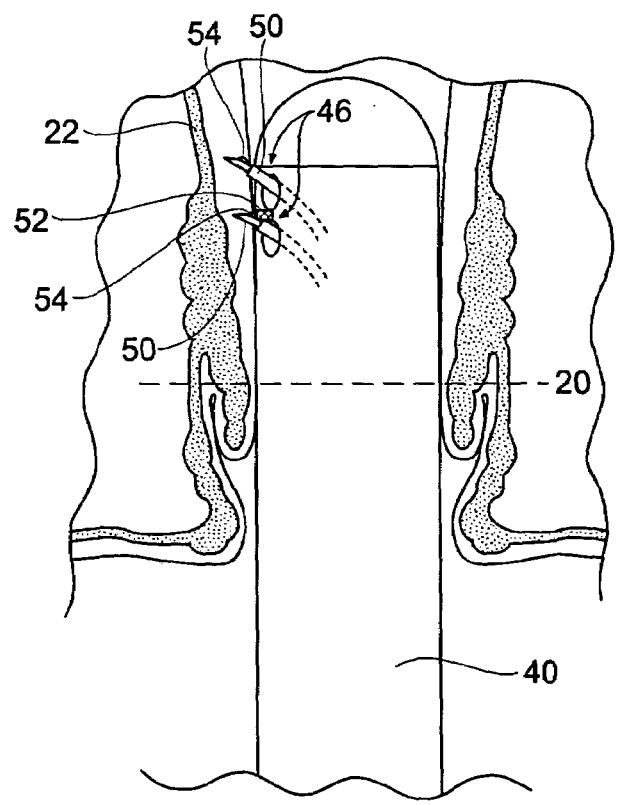
FIG. 10 is a view similar to FIG. 9 and illustrating the tissue-piercing members piercing tissue containing blood vessels that feed the internal and external hemorrhoidal plexes.

In an alternate embodiment, the operative element 38 carries an array of needle electrodes 46. The array of electrodes 46 is configured to deliver energy in a prescribed pattern to a targeted treatment site. It is contemplated that the number and placement of electrodes 46 can vary as needed for the desired procedure and to accommodate individual anatomy. FIGS. 9 and 10 illustrate an embodiment in which a pair of needle electrodes 46 is movably contained in a side-by-side relationship on the barrel 40.

The barrel 40 also preferably carries temperature sensor 52, one of which is associated with each needle electrode 46. The sensors 52 sense tissue temperature conditions in the region adjacent to each needle electrode 46. Preferably, the distal end of each needle electrode 46 also carries a temperature sensor 54.

In an optional embodiment, the treatment agent delivery apparatus 30 may convey processing fluid from a fluid source 34 for discharge at or near the treatment site. The processing fluid can comprise, e.g., saline or sterile water, to cool surface tissue while energy is being applied by the electrode 46 to thereby protect the surface tissue from thermal injury. For example, as seen in FIG. 6, barrel 40 may be coupled via tubing 35 to the fluid source 34 to convey fluid, e.g., through holes (not shown) in the barrel 40, to contact tissue at a localized position surrounding the electrodes 46. Alternatively, one or more electrodes 46 deployed by the operative element 38 can also be used to inject the fluid into the treatment site. In this arrangement, the electrode 46 includes an interior lumen (not shown) and the fluid source 34 is coupled to the lumen.

III. System Use

In use, the physician grasps the hand grip 36 and guides the barrel 40 into the anal canal 18 (see FIGS. 7 and 9). The pull lever 48 is in the neutral position and not depressed, so the needle electrodes 46 occupy their normal retracted position. Looking through the viewing port 44, the physician visualizes the pectinate (dentate) line 20 through the barrel 40. Looking through the barrel 40, the physician positions the distal ends of the needle electrodes 46 at a desired location above the pectinate (dentate) line 20, e.g., 2–4 cm above the dentate line 20. A fiberoptic can also be inserted into the barrel 40 to provide local illumination, or the physician can wear a headlamp for this purpose. In an embodiment where the barrel is not completely circumferential, but more U-shaped (thereby not occupying the entire anal canal 18), an endoscope or mirrors may be used to acquire visualization of the dentate line 20.

It may be desirable to bias the end of the treatment device 30 with a bend, to thereby facilitate contact with tissue in this region of the anal canal, as tissue in this region tends to be loose or flaccid. An expandable member may be desired to dilate tissue in this region in concert with use of the treatment device 30.

Once the distal end of the barrel 40 is located at the targeted site, the physician depresses the pull lever 48. The needle electrodes 46 advance to their extended positions (see FIGS. 8 and 10). The distal ends of the electrodes 46 pierce and pass through the mucosal tissue adjacent the targeted feeder vessel region without penetration of a hemorrhoidal plexus 24 or 26. The physician applies radio frequency energy through the needle electrodes 46. The energy can be applied simultaneously by all electrodes 46, or in any desired sequence, to apply energy in a selective fashion to a targeted feeder vessel region below mucusal tissue. The applied energy creates one or more lesions, or a prescribed pattern of lesions, below the mucosal surface. The electrodes 46 are then retracted, and the device 30 withdrawn.

Figure 11:
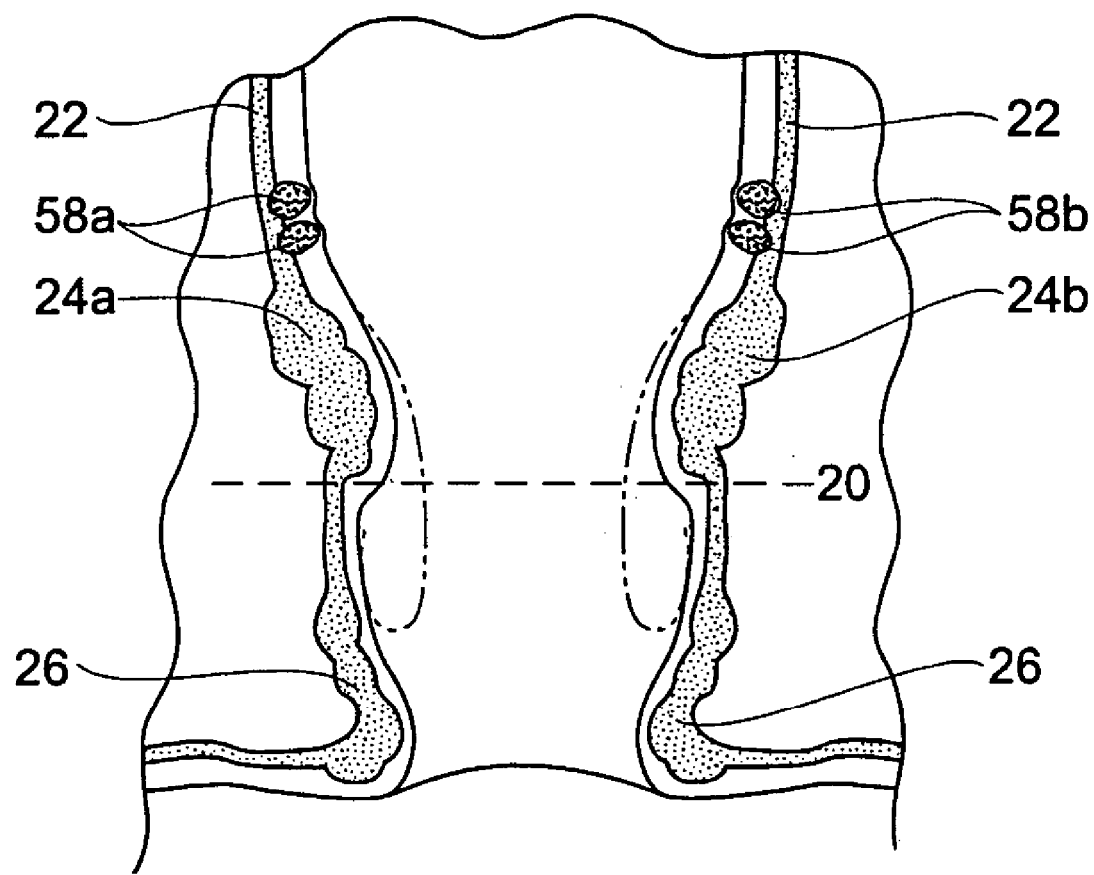
FIG. 11 illustrates the shrinkage of tissue in a feeder vessel region that occludes or otherwise reduces flow through the feeder vessels.

If desired, the process may be repeated to form a desired lesion pattern at a single location or at multiple locations. With the electrodes 46 in the retracted position, the operative element 38 may be rotated and/or axially advanced or retracted. The electrodes 46 are then advanced to their extended position and energy is again applied to form a lesion or series of lesions. The lesion pattern may be along a particular feeder vessel region for treatment of a single hemorrhoidal plexus 24 or 26. Alternatively, the lesions may be created in multiple feeder vessel regions for treatment of multiple hemorrhoidal plexes 24 or 26. For example, FIG. 11 illustrates the formation of a pair of lesions 58A in a first internal hemorrhoidal plexus 24A, and a second pair of lesions 58B in a second internal hemorrhoidal plexus 24B. As FIG. 11 also illustrates, the lesions 58A and 58B occlude or otherwise reduce, at least in part, blood flow through the feeder vessels 22 and thereby occlude or otherwise reduce the blood supply from above the hemorrhoidal plexes 24A and 24B. As a result, blood is essentially prevented from pooling in the vessels 22 and the hemorrhoidal plexes 24A and 24B. Since blood is prevented from pooling, hemorrhoids are shrunk or prevented. By targeting selected feeder vessel regions, the procedure can be adapted for the treatment of a single or multiple internal hemorrhoids, a single or multiple external hemorrhoids, or a combination of internal and external hemorrhoids.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method of treating hemorrhoids comprising
introducing a treatment device having at least one tissue piercing electrode into the anal canal adjacent a feeder vessel region spaced from a hemorrhoidal plexus and a dentate line, the feeder vessel region containing blood vessels that feed the hemorrhoidal plexus,
causing the at least one tissue piercing electrode to pierce and pass through mucosal tissue in the feeder vessel region without penetration of the hemorrhoidal plexus, and
operating the treatment device to apply radiofrequency energy to the feeder vessel region and not the hemorrhoidal plexus through the at least one tissue piercing electrode to create at least one lesion and shrink submucosal tissue in the feeder vessel region to occlude or otherwise reduce blood flow through the blood vessels that feed the hemorrhoidal plexus.

2. A method according to claim 1
wherein the at least one tissue piercing electrode is selectively advanceable into submucosal tissue and retractable from submucosal tissue.

3. A method according to claim 1
wherein the at least one tissue piercing electrode comprises an array of tissue piercing electrodes that creates a pattern of lesions in submucosal tissue.

* * * * *